United States Patent [19]

Lawson

[11] 4,185,680

[45] Jan. 29, 1980

[54] PROCESS FOR PRODUCING USEFUL CONCENTRATED SLURRIES FROM WASTE MATERIAL

[76] Inventor: Victor Lawson, Fetcham, England

[21] Appl. No.: 933,811

[22] Filed: Aug. 15, 1978

Related U.S. Application Data

[63] Continuation-in-part of Ser. No. 759,000, Jan. 13, 1977, abandoned.

[30] Foreign Application Priority Data

Jan. 28, 1976 [GB] United Kingdom ................. 3408/76

[51] Int. Cl.[2] ............................................... D21C 5/02

[52] U.S. Cl. .................................... 162/5; 48/197 A; 71/10; 71/12; 210/16; 210/68; 210/73 S; 426/807

[58] Field of Search ............. 48/197 R, 197 A; 71/10, 71/12-14; 210/2-6, 8-12, 14, 16, 66-68, 73 SG; 162/4, 5; 426/807

[56] References Cited

U.S. PATENT DOCUMENTS

| | | | |
|---|---|---|---|
| 2,572,767 | 10/1951 | Schlenz | 210/12 |
| 3,561,598 | 2/1971 | Goldberg | 210/10 |
| 3,655,046 | 4/1972 | Trussell | 210/73 SG |
| 3,736,223 | 5/1973 | Marsh | 162/4 |
| 3,774,760 | 11/1973 | Beristain et al. | 210/73 SG |
| 3,819,456 | 6/1974 | Enfield | 210/10 |
| 3,838,199 | 9/1974 | Coe et al. | 210/2 |
| 3,847,803 | 11/1974 | Fisk | 210/8 |
| 3,849,246 | 11/1974 | Raymond et al. | 162/4 |
| 3,981,800 | 9/1976 | Ort | 210/6 |
| 4,040,953 | 8/1977 | Ort | 210/6 |

*Primary Examiner*—Charles N. Hart

*Assistant Examiner*—Peter A. Hruskoci

*Attorney, Agent, or Firm*—Larson, Taylor and Hinds

[57] ABSTRACT

Domestic refuse containing inorganic and organic material is treated to separate off the inorganic material, after which the organic material, with sewage sludge, is assimilated in a digestor by a microorganism to produce a combustible gas, and a dilute slurry emerging from the digestor is dewatered to recover a self-binding concentrated slurry or cake containing long fibres suitable for use in the production of boards, paper, or fuel, for instance. The more dilute slurry which results from the dewatering is concentrated, and is then useful as a soil conditioner or animal feedstuff.

6 Claims, 2 Drawing Figures

FIG.I.

PROCESS FOR PRODUCING USEFUL CONCENTRATED SLURRIES FROM WASTE MATERIAL

CROSS REFERENCE TO PRIOR APPLICATION

This application is a continuation-in-part of Ser. No. 759,000 filed Jan. 13, 1977, now abandoned.

BACKGROUND OF THE INVENTION

This invention relates to a process for producing useful concentrated slurries from waste materials.

At present much domestic refuse is collected and taken a considerable distance from the point of collection to an area where it is used as a landfilling material. These filled areas, after allowing for settlement and after providing a layer of topsoil, can be used as playing fields or parkland.

Currently landfill sites in many areas are becoming filled, and new sites difficult to obtain. The generally used alternative to landfilling is incineration which is becoming expensive owing to high capital cost, involves compliance with many stringent environmental requirements and lacks the opportunity for recycling of useful material. With increasing transportation costs, it is desirable to minimize the quantity of material which needs to be transported. Also it is desirable to remove certain constituents of the waste material before disposing of the waste material.

Thus U.S. Pat. No. 2,572,767 (Schlenz) describes a process which involves diluting (with water) and grinding domestic refuse, separating off certain solids like metals, glass and bone, mixing the remainder (which is mainly organic material) with raw sewage sludge, treating the resulting mixture in a digestor where a microorganism produces a combustible gas like methane, burning part of the methane to produce heat for maintaining the digestor at the desired operating temperature, recycling part of the aqueous medium withdrawn from the digestor for use in the aforementioned dilution, and withdrawing a residue from the digestor. That patent, however, is silent regarding the fate of the withdrawn residue. Nonetheless there is disclosed in U.S. Pat. No. 3,838,199 (Coe) a process for recovering feed products from animal waste, in which a sewage sludge is treated in a digestor to produce methane which is burnt to heat the digestor, and in which a slurry withdrawn from the digestor is centrifuged to produce a cake which, when dried, can be used as or in an animal feedstuff.

Also, U.S. Pat. No. 3,847,803 (Fisk) discloses the handling of ground, diluted domestic refuse in which magnetic materials, glass and plastics materials are separated off before the remainder is treated in a digestor which produces a slurry which is centrifuged.

Rather then merely producing an animal feedstuff alone, the present invention has as its object the production of more useful products like boards for insulation, construction or packaging purposes, or fuel; although animal feedstuffs may be produced as a by-product.

SUMMARY OF THE INVENTION

According to the present invention there is provided a process for the production of a concentrated slurry containing long fibres suitable for use in the production of a self-binding product selected from the group consisting of paper, board and fuel, with the contemporaneous consumption of domestic refuse containing both organic and inorganic materials and of a sewage sludge, which process comprises:

diluting the domestic refuse with water and breaking up the refuse;

separating off from the diluted, broken-up refuse, the larger pieces of refuse containing the majority by weight of the inorganic material originally present in the refuse;

passing the diluted, broken-up refuse from which the larger pieces have been separated and which contains the majority by weight of the organic material originally present in the refuse, to a digestor containing microorganisms capable of assimilating the organic material present and of producing a hydrocarbon combustible gas;

passing to the digestor a sewage sludge;

allowing the microorganisms to feed on the sewage sludge and on said diluted, broken-up refuse from which the larger pieces have been separated, and to produce a hydrocarbon combustible gas;

burning part of the resulting combustible gas to provide the heat required to maintain the contents of the digestor at the required operating temperature;

withdrawing a dilute slurry from the digestor;

dewatering the dilute slurry withdrawn from the digestor in a manner such that the majority of long fibres are retained in the resulting first concentrated slurry with the long fibres entwined with each other to produce a self-binding product, there also being produced a more dilute slurry;

withdrawing the first concentrated slurry from the dewatering stage;

concentrating the said more dilute slurry to obtain a second concentrated slurry containing shorter fibres and other non-fibrous solid material, and to obtain a weak slurry;

withdrawing the second concentrated slurry which is suitable for use in or as a nutrient-bearing soil conditioner or animal feedstuff; and recycling said weak slurry to the digestor.

Conveniently the dewatering is effected on a moving perforated screen or belt, which retains the majority of long fibres present but allows to pass therethrough the shorter fibres, other solid material and water, there being a zone of subatmospheric pressure below the screen or belt.

Alternatively, the dewatering is effected in a press, which allows the retention of the majority of long fibres present, and allows the discharge of shorter fibres, other solid material and water.

The term "inorganic material" appearing in this specification is intended to cover all inorganic material present unless otherwise stated, but is not intended to include any water present.

Depending on the organic materials present in the digestor and on the choice of microorganisms, different combustible gases can be produced by the microorganisms. Whilst propane and butane could be produced, it is particularly convenient to produce methane.

Frequently the inorganic material in the refuse will contain magnetisable metals, hereinafter referred to as "ferrous metals", as well as non-magnetisable metals hereinafter referred to as "non-ferrous metals". It is to be understood that the "ferrous metals" can include magnetisable metals other than iron.

The majority by weight of the inorganic material separated off from the diluted, broken-up refuse can be subjected to magnetic separation, to separate off ferrous metals present, which can be baled or shredded as desired.

If there is any plastic material originally present in the refuse, the majority may be separated off from the diluted, broken-up refuse with the majority of the inorganic material. Much of this plastics material can be separated from the inorganic material in an air classifier which uses a blower. The recovered plastics material can then be baled or granulated, as desired.

The separated inorganic material, from which the ferrous metals and plastics materials have been separated, can be collected and used as a landfill material. This landfill material can weight approximately only one quarter of the original refuse, which can ensure a considerable saving in the transportation costs.

As will be explained hereinbelow in much greater detail, it may be preferred for economic reasons to have part of the plant for carrying out the process operating continuously and to have another part of the plant operating for only a portion of each day. In this case it might be necessary to have a buffer tank disposed upstream of the digestor, so that the portion of the refuse being passed to the digestor can collect in the tank during the aforementioned portion of the day and can be fed continuously to the digestor on a 24-hour per day basis.

Preferably the diluted, broken-up refuse passed to the digestor has a solids content in the range from 8 to 15 percent by weight.

If desired a raw sewage sludge can be fed to the buffer tank, which is kept stirred continuously, and the sludge in the resulting aqueous suspension forwarded to the digestor. None or some of the organic solids originally present in the sewage sludge may be assimilated by the microorganisms in the digestor. The sewage sludge can serve as a source of fresh microorganisms. The dilute slurry from the digestor is dewatered to produce a concentrated slurry which might have a solids content of, for example, 40% by weight and should contain the majority of long fibres present. This concentrated slurry can be used as a raw material in the production of paper or board for insulation, packaging or construction purposes, or as a fuel.

The dilute slurry from which the concentrated slurry has been separated is then itself concentrated, and the resulting slurry can be used as a basis for animal feedstuff subject to the removal of any dangerous constituents such as glass, metal or plastics material in a sorting step prior to digestion, or as a nutrient-bearing soil conditioner or peat substitute; this sorting step can be effected in a flotation apparatus, for example, a froth flotation tank, to remove glass and metals. The separated materials can then be passed to the stream of mainly inorganic material destined for landfilling purposes.

If desired, the aqueous medium for which said resulting slurry has been withdrawn can be sent to a tank provided with a stirrer, and part of the aqueous medium recycled to the aforementioned buffer tank. The remainder of the aqueous medium can be passed to a treatment plant and part of the resulting treated water can be recycled to be used as the water required to dilute the original refuse. Other parts of the resulting treated water can be discharged to the sewer.

The gaseous product of the digestor can include carbon dioxide in addition to methane or other combustible gas and this product can be treated to absorb and hence remove the carbon dioxide and to dry the remaining combustible gas which can then be pumped to a storage vessel and discharged from there for industrial use and for providing heat to maintain the content of the digestor at the desired operating temperature.

DESCRIPTION OF THE DRAWINGS

For a better understanding of the present invention and to show how the same may be carried into effect, reference will now be made, by way of example, to the accompanying drawings in which:

In FIG. 1 of the drawing there is shown a conveyor belt 1 for conveying refuse to a separating device 2 such as a wet pulping device for reducing the size of the solid materials present and for separating much of the solid material present from other material in the refuse. A pipe 3 is provided for conveying water to the device. The solid materials separated in the device 2 are conveyed by conveyor 4 to a magnetic separator 5 and any magnetisable material separated by the separator 5 is sent to a metal baler or shredder 6.

Figure 1:
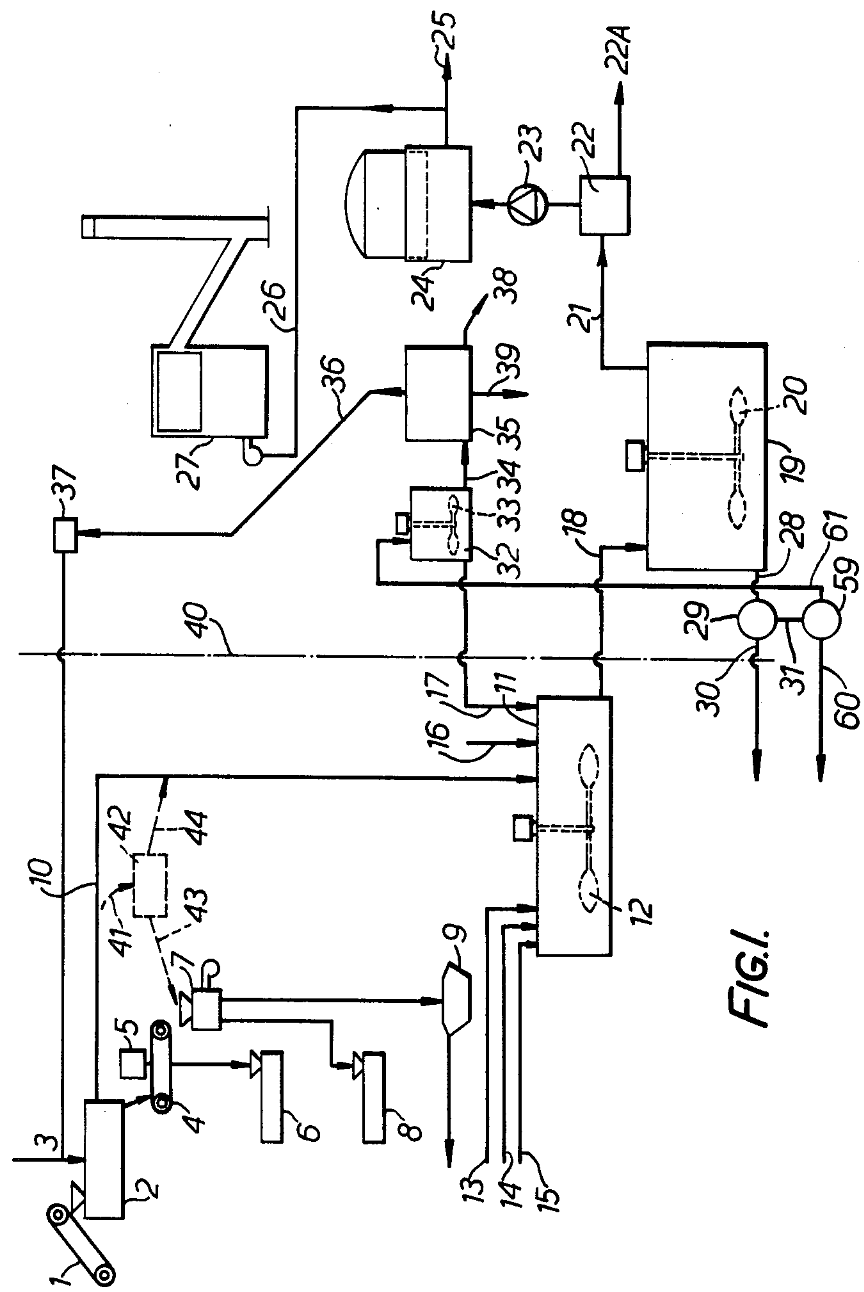
FIG. 1 shows in outline form a plant suitable for carrying out the process of the present invention.

The solid material from which the magnetisable material has been separated is transferred to an air classifier in the form of a blower 7 for separating off the plastics materials which are transferred to a baler or granulator 8. The remaining material is collected in a skip 9 and can be used as land fill.

The other material in the device 2, i.e. that not separated off towards the conveyor 4, is fed in a pipe 10 to a larger buffer tank 11 provided with a stirrer 12. Leading to the tank 11 are five pipes, namely a pipe 13 for feeding a raw sewage sludge to the tank 11, a pipe 14 for feeding water to the tank 11 during start-up, a pipe 15 used sometimes for feeding organic waste stream and liquid in proportion to the feed in pipe 10 to the tank 11, a pipe 16 for feeding pH control agents to the tank 11 and a pipe 17 for re-cycling centrate (described in detail below) to the tank 11.

A pipe 18 conveys slurry from tank 11 to a digestor 19 which is provided with a stirrer 20. In the digestor 19, microorganisms feed on the organic materials in the slurry and produce carbon dioxide and methane. These two gases are conveyed in a pipe 21 to a gas cleaning and drying station 22 where the carbon dioxide is removed by absorption and the remaining methane is purified and dried, any solid material being collected and discharged through a pipe 22A as a sludge which can be used as landfill.

The purified methane is pumped by a pump 23 to a storage vessel 24 from which part can be withdrawn through a pipe 25 for external use and from which part can be conveyed through a pipe 26 to a burner 27 used to generate heat required to maintain the slurry in the digestor 19 at the optimum temperature.

Slurry in the digestor 19 is withdrawn and transferred by a pipe 28 to a dewatering screen 29 for concentrating the slurry. The concentrated slurry, which contains the majority of the long fibres present, is discharged through a pipe 30 and can be used in the production of boards for construction, insulation or packaging purposes or for fuel.

The relatively dilute slurry from the dewatering screen 29 is conveyed in a pipe 31 to a second dewatering screen or press 59. The slurry which emerges from the screen or press 59 is discharged in a pipe 60 and can be used in the production of an animal feed or a nutrient-bearing soil conditioner. Aqueous effluent from the screen or press 59 is passed through a pipe 61 to a centrate tank 32 provided with a stirrer 33. Part of the centrate from the tank 32 is recycled via the aforementioned pipe 17 to the buffer tank 11 whereas the remainder is transferred via a pipe 34 to a treatment station 35. In the treatment station 35, the water is treated appropriately so that some may be recycled via a pipe 36 to a tank 37 and to device 2, some discharged to the public sewer through a pipe 38 and some discharged as slurry through a pipe 39 for landfill purposes.

If desired, the material being sent in pipe 10 from separator 2 to tank 11, can be sent via a pipe 41 to a froth flotation tank 42 to separate off glass and metals which can be transferred by conveyor 43 to blower 7, whilst the rest of the material is returned to pipe 10 via a pipe 44.

Part of the plant described above requires a work force and supervision and it could be arranged for this part to be operated eight hours per day, seven days a week. The other part of the plant could be arranged to operate automatically 24 hours per day, seven days a week, as it requires only minimal supervision and no labour force. In fact, those components numbered 1 to 10 and 13 to 17 could be operated only 8 hours per day, whereas the remaining components could be operated 24 hours per day. Thus, apart from the tank 11 and the stirrer 12, all components to the left of the broken line 40 in the drawing operate only 8 hours per day, and, apart from fluid flow through a pipe 17, all components to the right of the broken line 40 in the drawing operate 24 hours per day. Here, it will be appreciated that the microorganisms in the digestor 19 cannot satisfactorily be regulated to operate only an 8-hour day; in any case, it is more efficient to have this part of the plant operating all the time. Similarly, from the point of view of payment of the labour force, it is most efficient to have the part of the plant requiring a labour force operating for only 8 hours per day.

Figure 2:
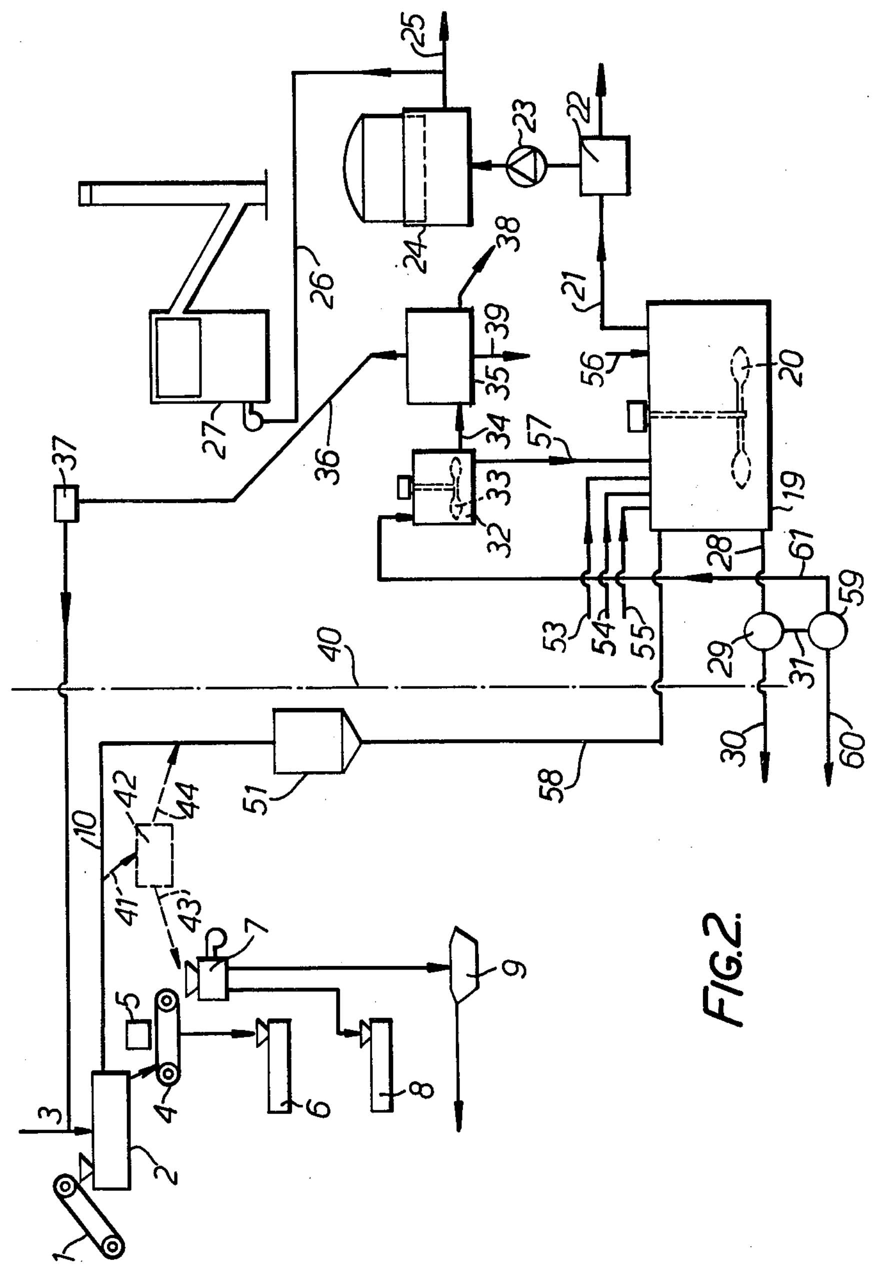
FIG. 2 shows in outline form a different plant for carrying out the process of the present invention.

Referring now to FIG. 2 of the accompanying drawings, the components 1 to 10, 19 to 44, 59, 60 and 61 therein are identical to the correspondingly numbered components shown in FIG. 1. In FIG. 1, however the pipe 10 (instead of leading to a buffer tank, as in FIG. 1) leads to a hopper 51 from the bottom of which a pipe 58 conveys waste to the digestor 19. Also leading to the digestor 19 are five other pipes, namely a pipe 53 for feeding raw sewage sludge, a pipe 54 for feeding raw sewage sludge during start-up, a pipe 55 used sometimes for feeding organic sludge and other liquid waste or sludges as required, a pipe 56 for feeding pH control agents, and a pipe 57 for recycling centrate. It can be seen that the pipes 53 to 57 correspond in function approximately to pipes 13 to 17 of FIG. 1. In the plant of FIG. 2 the hopper 51 replaces the buffer tank 11 of FIG. 1, and the pipes 53, 54, 55, 56 and 57 are now to the right of the broken line 40.

The present invention will now be illustrated by the following Example, in which references to tons are to Imperial tons, and references to gallons are to Imperial gallons.

EXAMPLE

The process described in this Example was carried out in a plant as illustrated in FIG. 1 of the drawing, with components 1 to 10 and 13 to 17 being in use 8 hours per day and the remaining components being in use 24 hours per day. The plant was operated 7 days a week for 50 weeks per year, and the annual tonnages given below are calculated on this basis.

Domestic refuse was fed to the conveyor 1 at a rate of 8 tons per hour, equivalent to 64 tons per day and to 22,400 tons per annum (with 7 day week and a 50-week year).

The composition of this domestic refuse fed to conveyor 1 was, in tons per hour, as follows:

| | |
|---|---|
| ferrous metals | 0.256 |
| non-ferrous metals | 0.256 |
| glass | 0.640 |
| other inorganic materials | 1.344 |
| plastics materials | 0.192 |
| other organic materials | 3.712 |
| water (inherent) | 1.600 |
| total | 8.000 |

Water was fed at a rate of 3.6 tons per hour to the device 2 via pipe 3, this being equivalent to a rate of 10,080 tons per annum. Thus the total quantity of water fed to the device 2 via conveyor 1 and pipe 3 was 5.200 tons per hour.

Most of the inorganic and plastics materials fed to the device 2 were separated off and fed to the conveyor 4; the remainder, which was fed through the pipe 10 to tank 11, had the following composition expressed in tons per hour:

| | |
|---|---|
| ferrous metal | 0.016 |
| non-ferrous metal | 0.016 |
| glass | 0.040 |
| other inorganic materials | 0.640 |
| plastics materials | 0.032 |
| other organic materials | 3.600 |
| water | 4.800 |
| total | 9.144 |

The materials fed to the conveyor 4 passed the magnetic separator 5 which separated off the majority of the ferrous material and forwarded it to a metal baler or shredder 6 which operated at the rate of 0.224 ton per hour, equivalent to 627.2 tons per annum.

The remainder of the material fed to the conveyor 4 was transferred to the air classifier which included the blower 7, which was responsible for separating off the majority of the plastics materials present. The latter were conveyed to a baler or granulator 8 which operated at the rate of 0.12 ton per hour, equivalent to 336 tons per annum.

The residue of the material, i.e. that not separated off by blower 7, was transferred to a skip 9 at the rate of 2.112 tons per hour, equivalent to 5,913 tons per annum and corresponding to 26.39% by weight of the refuse starting material. The composition of this residue in skip 9 was, on a ton per hour basis, as follows:

| | |
|---|---|
| ferrous metals | 0.016 |
| non-ferrous metals | 0.240 |
| glass | 0.600 |
| other inorganic materials | 0.704 |
| plastics materials | 0.040 |
| other organic materials | 0.112 |

-continued

| | |
|---|---|
| water | 0.400 |
| total | 2.112 |

This residue was suitable for direct use as landfill material.

The tank 11, in which the stirrer 12 operates 24 hours per day, has a capacity of 200,000 gallons and was capable of supplying the digestor 19 for 20 hours without addition of material through pipes 10, 13, 14, 15, 16 and 17, it being appreciated that these six pipes are out of operation 16 hours per day.

During the more active 8-hours part of the day, the tank 11 received, in addition to the material in pipe 10 (specified above), 7.3922 tons per hour of a 3% solids raw sewage sludge via pipe 13, water via pipe 14 (but only during start-up), pH control agents via pipe 16 and centrate recycled at the rate of 28.27 tons per hour for 8 hours per day via pipe 17. It was also possible to add via pipe 15 an organic sludge and liquid comparable in those in the refuse, but none was added in this Example.

From tank 11 to digestor 19 was fed via pipe 18 for 24 hours per day a mixture which had the following composition, expressed as tons per hour:

| | |
|---|---|
| ferrous metal | 0.0053 |
| non-ferrous metal | 0.0053 |
| glass | 0.0133 |
| other inorganic materials | 0.2133 |
| plastics materials | 0.0107 |
| sewage solids | 0.0739 |
| other organic materials | 1.2000 |
| water | 13.3853 |
| total | 14.9071 |

The digestor 19 was in the form of two chambers each having a capacity of 65,000 cubic feet. The stirrer 20 operated 24 hours per day. For efficient operation the digestor 19 required a heat input of 1,498,670 British thermal units (BTU) per hour, which heat was supplied by the burner 27.

From the digestor 19 were led off in pipe 21 carbon dioxide at the rate of 8,895 cubic feet per hour and methane at the rate of 8,824 cubic feet per hour. The carbon dioxide was separated off in the station 22 and other impurities were separated off and discharged through a pipe 22A as sludge for use as a landfilling material. The purified methane was pumped by pump 23 at the rate of 8,824 cubic feet per hour to the storage vessel 24 which thus received 211,776 cubic feet of methane per 24 hour day. This fuel intake is equivalent to $8.82\times10^6$ BTU per hour, or 88.24 therms per hour, corresponding to 741,216 therms per annum. The majority (approximately seven-ninths) of the methane was discharged through pipe 25 for external use (equivalent to 68.24 therms per hour, or 573,216 therms per annum), and 2,000 cubic feet per hour of methane was fed via pipe 26 to the burner 27, which was capable of providing $2\times10^6$ BTU per hour, where the methane was burned to provide approximately $1.5\times10^6$ BTU per hour used to heat the contents of the digestor 19.

From a bottom region of the digestor 19 were led off a dilute slurry which has a composition (expressed as tons per hour) identical to the mixture in pipe 18 except that the content of "other organic materials" had fallen from 1.2000 to 0.6047. Thus slurry was transferred via pipe 28 to the dewatering screen 29 which operated at approximately 54 gallons per minute. The dewatering screen 29 produced a 40% slurry which had the following composition expressed as tons per hour:

| | |
|---|---|
| ferrous metals | 0.0053 |
| non-ferrous metals | 0.0053 |
| glass | 0.0133 |
| other inorganic materials | 0.1100 |
| plastics materials | 0.0107 |
| sewage solids | 0.04434 |
| other organic materials | 0.5379 |
| water | 1.090 |
| total | 1.816 |

This 40% slurry in pipe 30 was produced in an amount of 43.584 tons per 24-hour day (calculated in the wet state), the latter being equivalent to 15,254 tons per annum. This slurry, which is self-binding in view of the intertwined long fibres, is ideal for use in the production of paper or board, or as fuel.

The effluent from the dewatering screen 29 was conveyed in a pipe 31 to the second dewatering screen or press 59 at a rate of 12.495 tons per hour, over a 24-hour day. This effluent had the following composition, expressed in tons per hour:

| | |
|---|---|
| inorganic material | 0.1329 |
| organic material | 0.0668 |
| water | 12.2953 |
| total | 12.495 |

The second dewatering screen or press produced a 40% solids slurry in pipe 60 which had the following composition expressed in tons per hour:

| | |
|---|---|
| inorganic material | 0.120 |
| organic material | 0.059 |
| water | 0.2685 |
| total | 0.4475 |

Tbhis 40% solids slurry was produced at the rate of 10.74 tons per 24-hour day (calculated in the wet state), the latter being equivalent to 3,759 tons per annum. This slurry is ideal for use in the production of an animal feed or nutrient-bearing soil improver, after removal of any metal, glass or plastics materials present; this slurry contains the majority of short fibres and other non-fibrous solid material. The effluent from the dewatering screen 59, was conveyed in pipe 61 at a rate of 12.047 tons per hour over a 24-hour day to the tank 32. This effluent had the following composition expressed in tons per hour:

| | |
|---|---|
| inorganic material | 0.012 |
| organic material | 0.006 |
| water | 12.029 |
| total | 12.047 |

The stirrer 33 in the tank 32 was operated continuously and the tank 32 had a capacity of 55,000 gallons and was thus able to receive centrate from pipe 61 for up to 20.4 hours. Much of the centrate in tank 32 was recycled via pipe 17 to buffer tank 11 at the rate of 28.1848 tons per hour for 8 hours per day; the remainder was sent via pipe 34 to the treatment station 35 at the rate of 2.6520 tons per hour over a 24-hour day. From the station 35 water was recycled at a rate of 1.2 tons per hour over a 24-hour day to tank 37 via pipe 36 and from there to pipe 3 at a rate of 3.6 tons per hour over an 8-hour day. Also from the station 35, 1.4520 tons per hour of waste material was discharged via pipe 38 to the sewer.

In summary, on an annual basis over a 50-week year, there were fed to the plant 22,400 tons of refuse, 10,080 tons of water and 20,700 tons of 3% sewage sludge, and there were obtained from the plant 627 tons of ferrous materials, 336 tons of plastics materials, 5,913 tons of landfill material, 15,254 tons of the 40% slurry having the majority of the long fibres, 3,759 tons of the 40% slurry having the majority of the short fibres, 22,276 tons of waste water (as measured in pipe 34) and 57,321,600 cubic feet of methane (equivalent to 573,216 therms per annum), as well as some carbon dioxide and small amounts of additional waste material.

Of the 22,276 tons of waste water, 10,080 tons were recycled to the device 2 and the remainder drained off.

When the slurry in pipe 60 is intended to be used as a basis for a nutrient-bearing soil conditioner or as an animal feedstuff, it is most practicable prior to the digestion to remove the metals, glass and plastics materials from the material being transferred from the device 2 to the tank 11, for example by use of the froth flotation tank 42. It will be appreciated that in the foregoing example, the process was carried out without employing such a tank 42.

The plant can be operated efficiently with the contents of the digestor 19 at a temperature in the range from 35° C. to 65° C., and in the case of the foregoing Example the temperature of the contents of the digestor was 60° C.

In the foregoing Example one of the microorganisms present in the digestor 19 was *Methanobacillus sp Omelianski.*

I claim:

1. A process for the production of a concentrated slurry containing fibers suitable for use in the production of a self-binding product selected from the group consisting of paper, board and fuel, with the contemporaneous consumption of domestic refuse containing both organic and inorganic materials and of a sewage sludge, which process comprises:

diluting the domestic refuse with water and breaking up the refuse;

separating off from the diluted, broken-up refuse, the larger pieces of refuse containing the majority by weight of the inorganic material originally present in the refuse;

passing the diluted, broken-up refuse from which the larger pieces have been separated and which contains the majority by weight of the organic material originally present in the refuse, to a digestor containing microorganisms capable of assimilating the organic material present and maintaining said digestor at a temperature effective for producing a hydrocarbon combustible gas selected from the group consisting of methane, propane, and butane;

passing to the digestor a sewage sludge;

allowing the microorganisms to feed on the sewage sludge and on said diluted, broken-up refuse from which the larger pieces have been separated and to produce said hydrocarbon combustible gas, the contents of the digestor being agitated to produce a uniform dilute slurry;

burning part of the resulting combustible gas to provide heat required to maintain the contents of the digestor at the required operating temperature;

withdrawing a dilute slurry from the digestor, said slurry containing long fibers of a length sufficient to produce a selfbinding product and fibers shorter than said long fibers;

dewatering the dilute slurry withdrawn from the digestor in a manner such that the majority of long fibers are retained in the resulting first concentrated slurry with the long fibers entwined with each other, there also being produced a more dilute slurry;

withdrawing the first concentrated slurry from the dewatering stage and drying said long fibers to produce said self-binding product;

concentrating the said more dilute slurry to obtain a second concentrated slurry containing said shorter fibers and other non-fibrous solid material, and to obtain a weak aqueous slurry;

withdrawing the second concentrated slurry which is suitable for use in or as a nutrient-bearing solid conditioner or animal feedstuff; and recycling said weak aqueous slurry to the digestor.

2. A process according to claim 1, wherein the dewatering is effected on a moving perforated screen or belt, which retains the majority of long fibres present but allows to pass therethrough the shorter fibres, other solid material and water, there being a zone of subatmospheric pressure below the screen or belt.

3. A process according to claim 1, wherein the dewatering is effected in a press, which allows the retention of the majority of long fibres present, and allows the discharge of shorter fibres, other solid material and water.

4. A process according to claim 1, wherein the concentration of the said more dilute slurry is effected by centrifuging.

5. A process according to claim 1, wherein the inorganic material contains a magnetisable metal which is separated by magnetic separation and then baled or shredded, and the refuse contains a plastics material which is separated off by air classification, the diluted, broken-up refuse passed to the digestor having a solids content in the range from 8 to 15% by weight.

6. A process according to claim 1, wherein the process is effected in a plant of which part generally operates for only a portion of each day and another part generally operates continuously.

* * * * *